United States Patent
Liu et al.

(10) Patent No.: US 11,144,576 B2
(45) Date of Patent: Oct. 12, 2021

(54) TARGET CLASS FEATURE MODEL

(71) Applicant: HEWLETT-PACKARD DEVELOPMENT COMPANY, L.P., Houston, TX (US)

(72) Inventors: Lei Liu, Palo Alto, CA (US); Anita Rogacs, Palo Alto, CA (US)

(73) Assignee: Hewlett-Packard Development Company, L.P., Spring, TX (US)

( * ) Notice: Subject to any disclaimer, the term of this patent is extended or adjusted under 35 U.S.C. 154(b) by 329 days.

(21) Appl. No.: 16/074,704

(22) PCT Filed: Oct. 28, 2016

(86) PCT No.: PCT/US2016/059556
§ 371 (c)(1),
(2) Date: Aug. 1, 2018

(87) PCT Pub. No.: WO2018/080522
PCT Pub. Date: May 3, 2018

(65) Prior Publication Data
US 2019/0034518 A1    Jan. 31, 2019

(51) Int. Cl.
*G06F 16/28* (2019.01)
*G16H 50/20* (2018.01)
(Continued)

(52) U.S. Cl.
CPC .......... *G06F 16/285* (2019.01); *G06F 16/288* (2019.01); *G16H 50/20* (2018.01); *G16B 40/00* (2019.02); *G16C 20/70* (2019.02)

(58) Field of Classification Search
CPC ..... G06F 16/285; G06F 16/288; G16H 50/20; G16C 20/70; G16B 40/00; G16B 20/00; G16B 40/20
See application file for complete search history.

(56) References Cited

U.S. PATENT DOCUMENTS 5,553,616 A * 9/1996 Ham .................. A61B 5/14558
600/316
7,990,532 B2    8/2011 Neiss et al.
(Continued)

FOREIGN PATENT DOCUMENTS

WO    2013028926 A2    2/2013

OTHER PUBLICATIONS

Richter et al., "Towards Many-class Classification of Materials Based on Their Spectral Fingerprints", Retrieved from Internet—http://publica.fraunhofer.de/eprints/urn_nbn_de_0011-n-3350044.pdf, Mar. 18, 2015, pp. 103-112.

(Continued)

*Primary Examiner* — Ashish Thomas
*Assistant Examiner* — Yohanes D Kelemework
(74) *Attorney, Agent, or Firm* — Rathe Lindenbaum LLP

(57) ABSTRACT

A method may include sensing first data samples from a first set of different subjects having a membership in a target class and sensing second data samples from a second set of different subjects not having a membership in the target class, wherein each of the first data samples and the second data samples includes a composite of individual data features. The individual data features from each composite of the first data samples and the second data samples are extracted and quantified. Sets of features and associated weightings of a target class model are identified based upon quantified values of the individual features from each composite of the first samples and the second samples to create a model representing a fingerprint of the target class to determine membership status of a sample having an unknown membership status with respect to the target class.

17 Claims, 5 Drawing Sheets

(51) Int. Cl.
*G16C 20/70* (2019.01)
*G16B 40/00* (2019.01)

(56) References Cited

U.S. PATENT DOCUMENTS

| | | | |
|---|---|---|---|
| 8,541,170 | B2 | 9/2013 | Kennedy et al. |
| 9,082,083 | B2* | 7/2015 | Virkar .................... G06N 20/10 |
| 9,265,441 | B2 | 2/2016 | Pereira et al. |
| 9,638,656 | B2* | 5/2017 | Malecha ................ G01N 27/26 |
| 2003/0185436 | A1* | 10/2003 | Smith .................. G06K 9/6232 |
| | | | 382/159 |
| 2003/0186461 | A1* | 10/2003 | Boehr ................ G01N 33/0034 |
| | | | 436/181 |
| 2005/0209785 | A1* | 9/2005 | Wells ..................... G16H 50/20 |
| | | | 702/19 |
| 2011/0178718 | A1 | 7/2011 | Henriquez et al. |
| 2012/0078523 | A1 | 3/2012 | Letant et al. |
| 2012/0252050 | A1 | 10/2012 | Towler et al. |
| 2014/0038850 | A1* | 2/2014 | Fasan ................. C12N 15/1093 |
| | | | 506/11 |
| 2014/0302492 | A1 | 10/2014 | Blackburn et al. |
| 2015/0066377 | A1 | 3/2015 | Parchen et al. |
| 2016/0292197 | A1* | 10/2016 | Morimoto ............. G06F 16/285 |

OTHER PUBLICATIONS

Butler, Holly J. et al. "Using Raman spectroscopy to characterize biological materials." Nature protocols 11, No. 4 (2016): 664.
Gautam, Rekha et al. "Review of multidimensional data processing approaches for Raman and infrared spectroscopy." EPJ Techniques and Instrumentation 2, No. 1 (2015): 1-38.

* cited by examiner

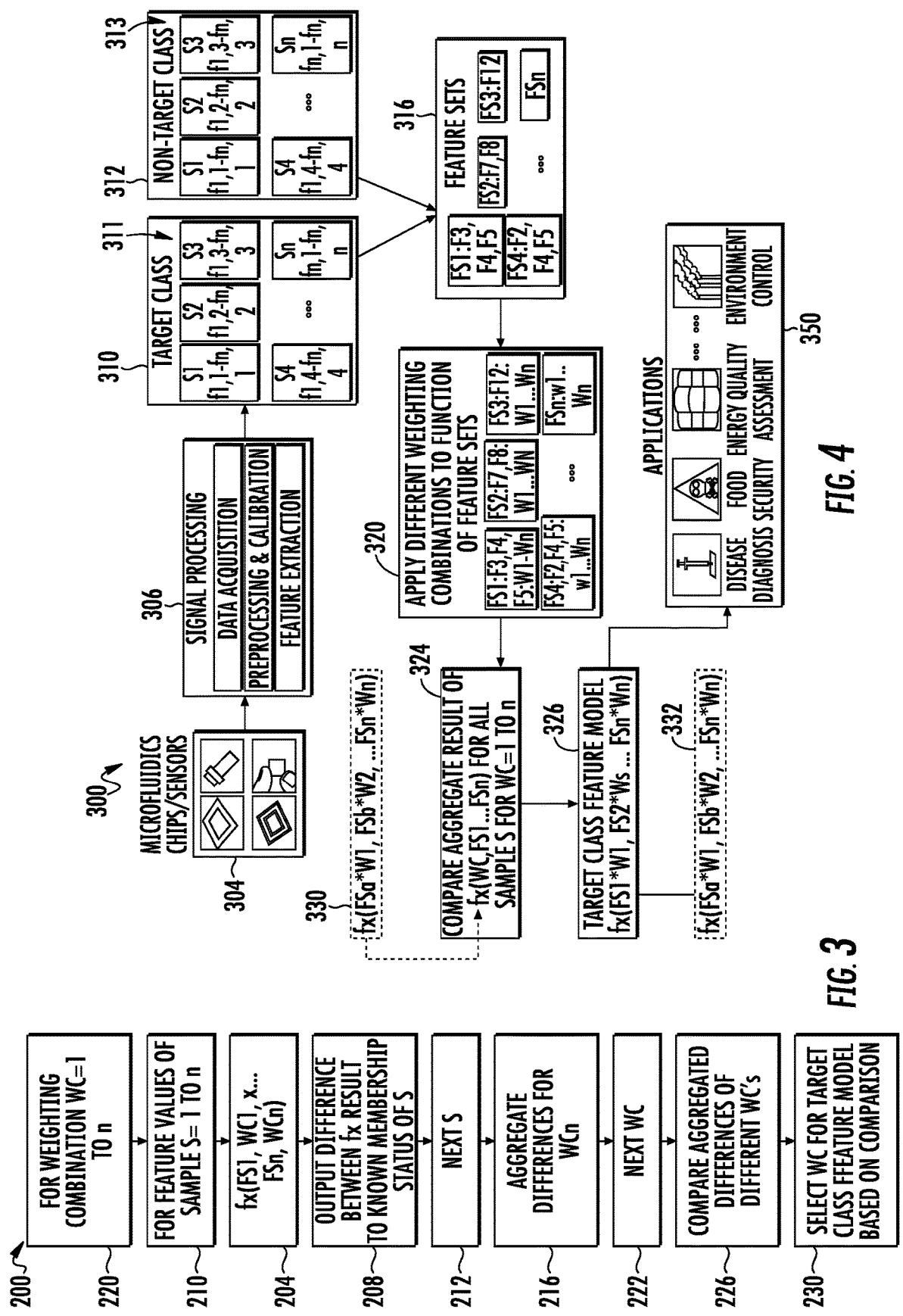

TARGET CLASS FEATURE MODEL

BACKGROUND

Diagnostics are utilized to identify or determine whether a subject belongs to a specified class or has a specified condition. For example, diagnostics are utilized in life sciences to determine whether a subject may have cancer. Diagnostics may be utilized to identify whether a subject is authentic or a counterfeit. Diagnostics may be utilized to evaluate food security, energy quality or environmental conditions.

BRIEF DESCRIPTION OF THE DRAWINGS

FIG. 3 is a flow diagram of an example implementation of the method of FIG. 2 for generating a target class feature model.

FIG. 4 is a diagram of an example method for generating a target class feature model.

DETAILED DESCRIPTION OF EXAMPLES

Figure 1:
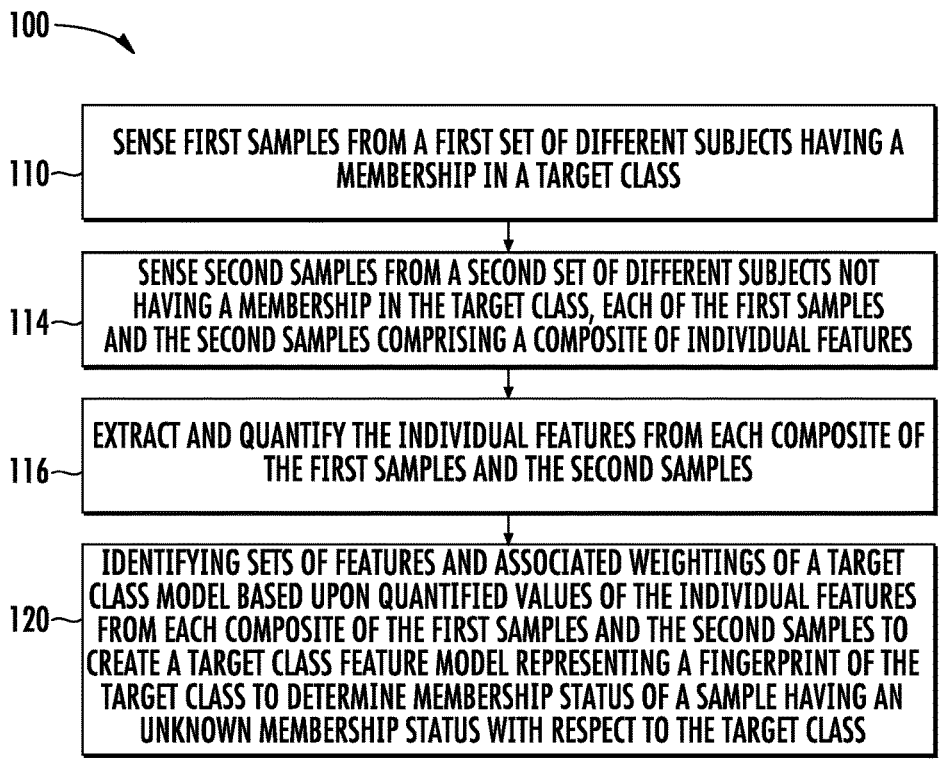
FIG. 1 is a flow diagram of an example method for generating or creating a target class feature model.

Existing diagnostic techniques or methods are often binary in nature, indicating whether a subject belongs to a class or has a condition, or does not belong to the class or does not have the condition. Examples of different classes to which a subject might belong or a condition/status which a subject may possess include: a particular health condition or disease; a particular environmental condition, the state of being authentic or the state of being counterfeit, a safe or an unsafe condition for food or the like, or a level of quality regarding a product or resource. Many existing diagnostic methods do not provide insights as to the nature and source or causes of a condition or diagnosed state. Existing diagnostic methods are often complex, unreliable and difficult to adapt to new data or new influences.

Disclosed herein are examples of methods for creating, using and updating a target class feature model that may offer greater reliability, adaptability to new data or new influences and deeper insights into contributors to an identified condition or membership status with respect to a class. Disclosed herein is an example database resulting from the example methods. The Example database identifies individual features or combinations of data features that may exist in a data sample and that may indicate membership in a class. For example, an example database may identify individual data features or combinations of data features from a biological data sample that tend to indicate the presence of a disease or other condition. Disclosed herein are further example methods that identify what particular chemicals or combinations of chemicals correspond to the individual data features or combination of data features that indicate membership in a class, providing insight as to the causes or chemical contributors towards membership in a class. For example, the disclosed methods may indicate particular chemicals or combination of chemicals associated with sample data features or samples groups of data features that indicate cancer.

Disclosed herein is an example method that utilizes "ground truth samples" by sensing and obtaining first data samples from a first set of different subjects having a membership in a target class and sensing and obtaining second data samples from a second set of different subjects not having a membership in the target class. Each of the first data samples and the second data samples comprising a composite of individual features. The individual features from each composite of the first data samples and the second data samples are extracted and quantified. In some implementations, feature sets may be created and formed from functions of combinations of selected individual features (a subset of all of the individual features). Sets of data features and associated weightings of a target class feature model are identified based upon quantified values of the individual features from each composite of the first data samples and the second data samples to create a target class feature model representing a fingerprint of the target class to determine membership status of a sample having an unknown membership status with respect to the target class.

Disclosed herein is an example non-transitory computer-readable medium. The medium contains instructions to direct a processor to: receive a composite of data features from each data sample of first data samples having a membership in a target class; receive a composite of data features from each sample of second data samples not having a membership in the target class; and extract and quantify individual data features from each composite of the first samples and the second samples. The medium contains instructions to direct the processor to further iteratively apply different candidate weighting combinations to feature sets to create a different candidate model during each iteration. For each iteration, the different candidate model is applied to the extracted and quantified individual features from each composite of the first data samples and the second data samples. The result of each different candidate model applied to the extracted and quantified individual features from each of the first samples and the second samples is compared to a known membership status of each of the first data samples and the second data samples. The target class feature model representing the fingerprint of the target class based upon composites of individual features is selected based upon the comparison.

Disclosed herein is an example database. The database comprises a class and sets of sensed data features. Each set of the sensed data features has a weight indicating a relevance of the set of data features towards identifying membership of a subject with respect to a class. Such a database may facilitate quicker and more reliable diagnosis of a condition or class membership.

FIG. 1 is a flow diagram of an example method 100 for generating a target class feature model that may serve as a fingerprint for a target class to assist in determining membership status of a sample having an unknown membership status with respect to the target class. As indicated by block 110, data samples from a first set of different subjects having a membership in a target class are sensed. As indicated by block 114, data samples from a second set of different subjects not having a membership in the target class are also sensed. The data samples from the first set of subjects and the second set of subjects serve as a ground truth for subsequent analysis. Each data sample comprises a data sample from which multiple individual features may be extracted.

A sample is a set of sensed data taken from a subject. In one implementation, a sample may comprise impedance data. In another implementation, a sample may comprise Raman spectroscopy data. In some implementations, different samples may comprise similar samples measured with different Raman spectroscopy enhancement surfaces.

Features of a data sample may comprise individual characteristics or aspects of the data in the sample. For example, in the case of Raman spectroscopy data, a feature may comprise individual aspects or characteristics of the spectra data based upon an amplitude, duration, frequency, or timing of the spectral peaks of the Raman spectra data. Other specific examples of different individual features may include, but are not limited to, maximum peak amplitude, peak amplitude at a predetermined time, a statistical value based upon a plurality of peak characteristics, a peak to peak ratio, and all other types of created features through a feature engine, such as deep learning, Principal Component Analysis (PCA) and the like.

As indicated by block 116, individual features in the composite set of features forming the sample are extracted and quantified in each of the first samples belonging to the target class and each of the second samples not belonging to the target class. For example, with respect to Raman spectroscopy data samples, the amplitude, location, frequency, duration and other values regarding the peaks or other characteristics of the Raman spectra may be measured or otherwise obtained. The values of the measurements are subsequently utilized in combination (a function of multiple individual features) with various potential or candidate feature weightings to identify what specific weightings should be applied to specific feature sets of a function. The function may comprise any formula or the like in which the different feature sets, multiplied by their respective associated weightings, serve as variables in the function. For example in one implementation, the function may be a multivariable equation in which the different feature sets, multiplied by their and their respective associated weightings, are added. As should be appreciated, the exact features for which values or measurements are taken may vary depending upon the type of data samples being taken.

As indicated by block 120, sets of data features and their associated weightings or applied weights for a target class feature model (a function of the sets of features and their associated weightings) are identified based upon the quantified values of the individual features from each composite of the first samples of the second samples. In other words, feature sets comprising an individual feature or a combination of individual features (combined as part of a function) from the different samples serve as variables in a function that identifies whether the sample belongs to a target class or does not belong to a target class. A feature set may be an individual feature or a created function of a combination of individual features. Each feature set is assigned a weighting factor. The selection of the weighting factor, applied to each of the feature sets in the function, influences the accuracy of the function in properly identifying the sample as belonging to the class or not belonging to the target class. A combination of weighting factors is the value of the weighting factor as well as a particular feature set of the function to which the weighting factor is associated.

In block 120, the method 100 determines the particular combination of weighting factors for the feature sets in the function/model that achieves the desired objective such as most accurately predicting whether a sample belongs to a class, such as reducing the occurrence of false positives or such as reducing the occurrence of false negatives in the predicted outcome. Method 100 determines the particular combination of weighting factors by "plugging in" the quantified or measured values for each of the feature sets in a sample into the function of the feature sets and associated weighting factors. For example, for a first sample, its measured value for feature 1 is plugged into the function variables that comprise feature 1 or that are based at least in part upon feature 1. For a second sample, its measured value for feature 1, which may be different than the value of feature 1 in the first sample, is plugged into the function variables that comprise feature 1 or that are based at least in part upon feature 1. Due to the different plugged in measured or quantified values from each sample, the function may yield different results. For each sample, the results of the function, indicating/predicting whether or not the specific sample belongs to the target class, are compared to the actual "ground truth" for the specific sample.

This process is repeated for each of the first ground truth samples and the second ground truth samples. For each combination of different weighting factors applied to the different feature sets of the function, a prediction accuracy or indication accuracy is determined. For example, one candidate model having a first combination of weight factors applied to the feature sets may be more accurate as compared to a second candidate model having a second different combination of weighting factors applied to the same feature sets. The model having the particular combination of weight factors applied to the feature sets that has a highest accuracy (the indication result of the model most frequently being the same as the ground truth membership status) may be identified as the target class feature model.

Figure 2:
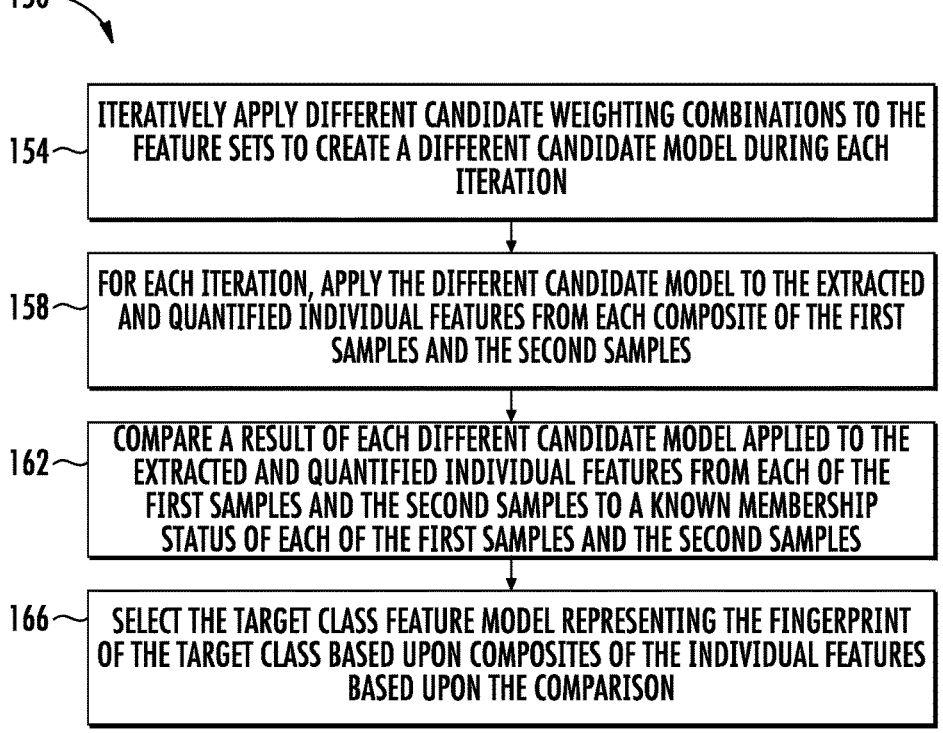
FIG. 2 is a flow diagram of an example method for generating a target class feature model through the iterative application of different weighting combinations and the use of ground truth sample feature values.

FIG. 2 illustrates an example method 150 for identifying the combination of weightings or weighting factors that form the target class feature model. FIG. 2 illustrate an example method 150 for carrying out block 120 in method 100. As indicated by block 154, different potential or candidate weighting combinations are iteratively applied to the feature sets of the function to create a different candidate model during each iteration. For example, during a first iteration, a first candidate model may comprise $fx(W_1FS_1, W_2FS_2 \ldots W_n,FS_n)$, wherein $W_1 \ldots W_n$ are weighting factors and wherein $FS_1 \ldots FSn$ are feature sets. During the second iteration, a second candidate model may comprise the exact same function with the exact same feature sets, but wherein at least some of the individual feature sets have different associated weighting factors as compared to the first iteration. For example, the second candidate model may comprise $fx(W_1'FS_1, W_2'FS_2 \ldots W_n', FS_n)$, wherein at least one of $W_1' \ldots Wn'$ is a weighting factor different than its corresponding respective weighting factor $W_1 \ldots W_n$.

As indicated by block 158, during each iteration, the current candidate model is evaluated for accuracy using the actual measured values for the feature sets of the function taken from the first and second samples forming the ground truth samples. For each iteration, method 150 applies a different candidate model to the extracted and quantified individual features from each composite of the first samples and the second samples. For example, the measured values for the individual features forming the feature sets are plugged into the candidate model of each iteration containing a particular combination of weighting factors, wherein the candidate model outputs a result for the candidate model predicting whether the current sample is a member or is not a member of the class.

As indicated by block 162, the result of each different candidate model applied to the extracted and quantified individual features from each of the first samples and the second samples is compared to a known membership status of each of the first samples in the second samples. For example, for a first sample from the first set of subjects having a membership in the target class, the accuracy of the results of output by each candidate model towards properly indicating the sample as being a member of the target class is evaluated or determined. Likewise, for a second sample from the second set of subjects known to not have a membership in the target class, the accuracy of the results of the output by each candidate model towards properly indicating the sample is not being a member of the target class is evaluated are determined. This process is repeated for each sample, wherein the aggregate accuracy results of each candidate model may be compared against one another. As indicated by block 166, the candidate model (with its associated particular weighting combinations) having the highest degree of accuracy may be selected as the target class feature model, representing the fingerprint of the target class based upon composites of individual features. The highest degree of accuracy serving as a criteria for selecting which of the candidate model 50 serve as a target class feature model may vary depending upon the objectives such as generating a target class feature model having the fewest number of false positives, generating a target class feature model having the fewest number of false negatives, or generating a target class feature model that most accurately indicates or predicts whether a sample belongs to a target class.

FIG. 3 is a flow diagram of an example method 200, an example implementation of method 150. FIG. 3 illustrates the iterative nature of method 150 in the form of "For . . . Next loops". As indicated by block 204, the results of a function fx is determined, wherein the function has a set of variables in the form of feature sets $FS_1 \ldots FS_n$ and wherein each of the variable/feature sets FS has an associated weighting factor of a particular weighting combination WC. The result of the function fx for an individual sample is determined by using the measured or quantified values for their associated variables, the feature sets that may comprise the values for an individual feature or the values based upon a combination of values for features.

As indicated by block 208, the result of the function has a value, based upon a predetermined scale, that indicates whether or not the particular sample belongs to a target class or does not belong to a target class. This result is compared against the ground truth, the predetermined membership status of the sample with respect to the target class. For example, in one implementation, a positive numerical result between zero and one may indicate membership in the target class or a negative numerical result between zero and −1 may indicate a lack of membership with respect to the target class. A sample predetermined to be within the target class (the first set of different subjects) will have a ground truth value of 1 while a sample predetermined to not be within the target class (the second set of different subjects) will have a ground truth value of −1. For each result determined in block 204, a difference between the result in the ground truth value for the sample is determined and output. Such differences are stored and subsequent utilized to evaluate the accuracy of the particular combination of weighting factors forming the candidate model applied in block 204.

As indicated by for-next loops of blocks 210 and 212, respectively, blocks 204 and 208 are repeated for each sample of the ground truth set of samples, the first set of subjects having a membership in the target class and the second set of different subjects not having a membership in the target class.

As indicated by block 216, the differences output in block 208 for each sample S for the current a respective weighting combination WC are aggregated. The aggregating constitutes a statistical or functional result of all of the individual differences for the individual samples. In one implementation, the aggregation may comprise the summing of each of the differences to yield a total difference value for all of the samples S for the particular weighting combination WC. In another implementation, aggregation may comprise determining an average or mode of the set of different values that resulted from the feature sets of the function fx being applied with the particular weighting combination WC. In yet other implementations, aggregation may comprise yet another form of aggregation based upon the total number or collection of difference values for all the samples for the particular weighting combination WC. In some implementations, outer extreme difference values may be culled from the aggregation.

As indicated by the for-next loop of blocks 220 and 222, blocks 204, 208, 210, 212 and 216 are repeated once again for each potential or candidate weighting combination WC. In one implementation, the number of different weighting combinations, the resolution of the weights of the different weighting combinations and/or the distribution of the different weights or various assignments of the different weights with respect to the different feature sets may be optimized using various optimization techniques such as global optimization or kernel optimization using various optimization techniques such as convex optimization, concave optimization and the like.

As indicated by block 226, the aggregated differences for each candidate weighting combination WC, as determined in block 216, are compared. As indicated in block 230, the combination of weighting factors WC satisfying a predefined objective or predefined level of accuracy is selected for generating the target class feature model based upon the comparison. For example, in one implementation, the combination WC of weighting factors having the smallest aggregation of differences across all of the ground truth samples may be selected as the combination WC of weighting factors for generating the target class feature model.

The target class feature model generated or determined is the function fx of the multiple feature sets with the particular selected combination of weighting factors WC applied thereto. For example, an example target class feature model might comprise $fx(W_2*FS_1, W_5*FS_2, W_5*FS_3, W_{41}*FS_4 \ldots )$, where the particular combination of the values for weighting factors W2, W5, W4 as well as their particular assignment to the respective feature sets FS produced the smallest aggregate difference across all of the ground truth samples as compared to other weighting factor values in other particular assignments of weighting factor values to particular feature sets FS.

FIG. 4 is a diagram of an example method 300 an example implementation of method 100, method 150 and/or method 200. As indicated by block 304, ground truth samples are first obtained or received. Such ground truth samples include samples from subjects having a known membership in a target class as well as samples from subjects having a known membership not in the target class. Each sample may comprise a collection of data corresponding to multiple individual features or a composite of multiple individual features. In one implementation, each sample may be sensed on a microfluidic chip or using a microfluidic sensor. In one implementation, each sample may comprise impedance data. In another implementation, each sample may comprise Raman spectroscopy or surface enhanced Raman spectroscopy spectra data.

As indicated by block 306, signal processing is carried out on the sample data. Such signal processing involved data acquisition, preprocessing and calibration as well as feature extraction. Feature extraction involves the identification of individual characteristics or aspects of the data from months other characteristics or aspects of the data. Such feature extraction further involves the quantification or measurement of each individual feature.

Features of a sample may comprise individual characteristics or aspects of the data in the sample. For example, in the case of Raman spectroscopy data, a feature may comprise individual aspects or characteristics of the spectra data based upon an amplitude, duration, frequency, or timing of the spectral peaks of the Raman spectra data. Other specific examples of different individual features may include, but are not limited to, maximum peak amplitude, peak amplitude at a predetermined time, a statistical value based upon a plurality of peak characteristics, a peak to peak ratio, and all other types of created features through a feature engine, such as deep learning, Principal Component Analysis (PCA) and the like.

As illustrated by blocks 310 and 312, the result of the feature extraction is a collection of ground truth samples: ground truth samples 311 for the target class and ground truth samples 313 for the non-target class. For example, one target class might be samples taken from subjects known to have a particular disease whereas the non-target class might be samples taken from subjects known to not have the same particular disease. As further shown by blocks 310 and 312, the samples from both the target class 311 and the nontarget class 313 are taken using the same acquisition methods such that the same individual features are present in each of the samples. In the example illustrated, each sample acquired during the sensing in block 304 and output by the signal processing and feature extraction and 306 comprises individual features $f_1 \ldots f_n$.

As illustrated by block 316, feature sets FS are identified from the individual samples for inclusion in a function fx that outputs a value to be used for indicating whether or not the sample has a membership in a target class or a membership outside the target class. In one implementation, the function may comprise all of the individual features found in each of the samples of the ground truth samples as well as all of the different combinations of features, combined through a separate function in which the combined features serve as variables in the separate function. In one implementation, a feature creation or generation engine, a module of processor instructions and a processing unit, may identify and generate different combinations or different functions of multiple individual data sample features that serve as feature sets (variables) in the sample predicting function. The feature creation or generation module creates multi-feature feature set variables using global optimization techniques. In on implementation, In another implementation, a selected portion of the total number of possible combinations of individual features is included in the function. In one implementation, the number of possible combinations or the selection of the different combination of individual features is carried out using global optimization or kernel optimization/distance metric learning.

As indicated by block 320, different weighting combinations are applied to the feature sets 316 of the function. As described above with respect to method 200, different combinations of weighting factors are applied to the feature sets of the function, iteratively. As indicated by blocks 204, 208, 210 and 212, the quantified or measured values for each of the feature sets of each of the samples are used for the corresponding feature set variables in the function to determine a difference between the function result and the ground truth value for each sample for each different weighting combination.

As illustrated by block 324 and described above with respect to block 216, the differences for each individual weighting combination across all of the ground truth samples are aggregated. As described above with respect to block 226, the aggregated differences of each weighting combination (WC=1 to n) are compared. As described above with respect to block 230, a particular weighting combination is selected for generation of the final target class feature model 326.

As illustrated in broken lines, in some implementations, the individual feature sets of each candidate function or candidate model may itself be the result of a secondary or lower level function 330 of a selected portion of or combination of individual features and associated secondary weighting factors. For example, the feature set $FS_1$ in the candidate function or candidate model (the primary function) may itself have a value that is the result of a secondary function of a first feature set $FS_a$ multiplied by its corresponding weighting factor $W_1$, a second feature set $FS_b$ multiplied by its corresponding weighting factor $W_2$ and so on. In such implementations, the different weighting combinations (as described above with respect to blocks 220 and 222) may also include different weighting combinations for the secondary functions. For example, the value for $FS_1$ in the primary function may have multiple different values in different iterations even though the quantified values of the secondary individual features that serve as variables for the secondary function providing the value for $FS_1$ remain the same, due to the different weighting factors applied to the different secondary individual features as the different weighting combinations are iteratively applied.

As further indicated by broken lines, the final target class feature model 326 may comprise a primary class indicating function that itself includes feature sets having values resulting from secondary functions 332 of a selected portion of the total number of possible individual features with a selected weighting combination that reduces error. In still other implementations, the feature sets ($FS_a$, $FS_b$ and so on) of the secondary function may themselves have values resulting from yet further lower level functions (not shown) of selected individual features with selected weighting combinations.

As indicated by block 350, once the final target class feature model 326 has been generated using the selected weighting combination for the feature sets of the sample indicating function, samples from subjects having an unknown membership status respect to the target class 311 may be evaluated to predict class membership. For example, a sample may be taken from a patient to determine whether or not the patient belongs to a target class, whether or not the patient has, for example, cancer. The sample may be sensed. The various individual features of the data sample may be extracted and quantified and used as values for the various features set variables of the target class feature model to provide an output indicating membership status of the sample. In some implementations, computation complexity and feature extraction complexity may be reduced by extracting and quantifying a portion of the total number of individual features, such as by extracting and quantifying those individual features having corresponding weighting factors F greater than a predefined weighting value or weighting threshold. For example, individual features that are only associated with extremely low weighting factors W (below a predefined cutoff threshold) may be ignored for sake of cost or expediency. As further shown by block 350, the samples to which the target class feature model 326 is applied may be used to diagnose disease, food security or contamination, energy quality or environmental conditions, amongst others.

Figure 5:
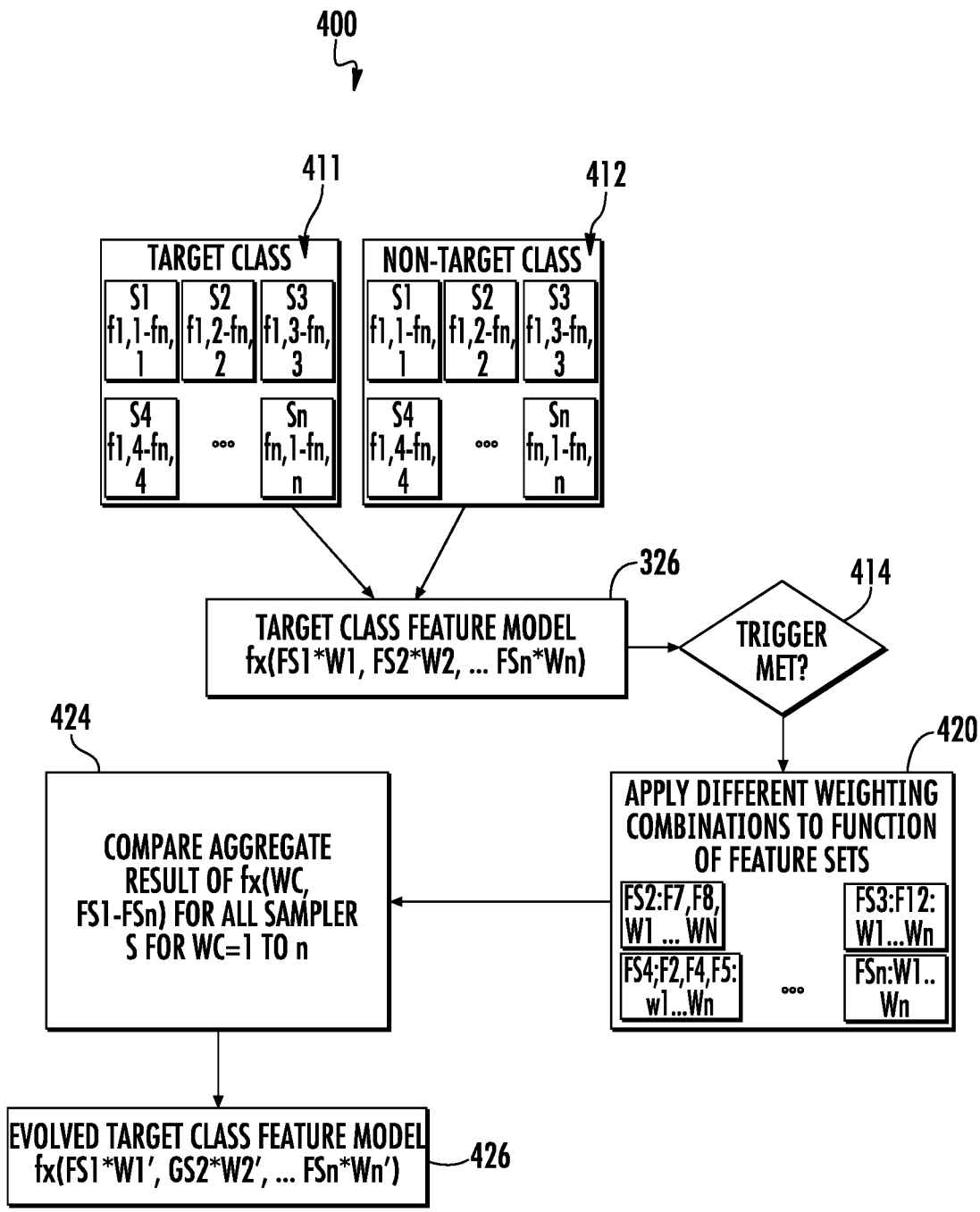
FIG. 5 is a diagram of an example method for updating a previously generated target class feature model using new round truth data samples.

FIG. 5 is a diagram illustrating the evolving of a target class feature model to automatically adapt to changing contributors or changing factors to a condition or membership status over time. FIG. 5 illustrates an example method 400 for automatically updating the target class feature model 326 (shown in FIG. 4). As shown by FIG. 5, additional ground truth samples for 11 and 412 may be obtained or sensed over time. The individual features of each ground truth sample are extracted and quantified as described above respect to block 116 of method 100. The extracted and quantified values for each of the individual features of an individual sample are then inserted into the target class feature model 326 for the respective feature sets of the model 326. If the result of the target class feature model applied to the individual sample is sufficiently close to the ground truth value for the same individual sample, no updating is carried out. For example, if the sample is in the target class 411 with the ground truth value of +1 and the result of the insertion of the values for the sample into the target class feature model result in an output of a positive value (also indicating membership in the target class 411), a decision that no updating may be made. As should be appreciated, in other implementations, the threshold value for triggering the updating of the target class feature model may not necessarily be equally distantly spaced between the ground truth value for target class membership and the ground truth value for being outside of the target class.

By way of contrast, if the result of the target class feature model applied to the individual sample is incorrect or is not sufficiently close to the ground truth value for the same individual sample, an update to the existing target class feature model may be triggered as indicated by decision block 414. As indicated by block 420 and block 424, the processes described above with respect to blocks 320 and 324, respectively, are repeated with the addition of the new or additional ground truth sample or group of new or additional ground truth samples to the classes 311 and 313 for once again evaluating the different weighting combinations to determine which particular weighting combination, when applied to the different feature sets of the sample indicating function has an acceptable degree of accuracy. As illustrated by FIG. 5, the inclusion of the new subsequently sensed and acquired ground truth sample or samples may result in the selection of a different weighting combination and the generation of a different "evolved" target class feature model having the different weighting combination applied to the same feature sets. In the example illustrated, the evolved target class feature model 426 may have at least one weighting factor $W_1'$, $W_2'$ ... $Wn'$ which is different than its corresponding weighting factor $W_1$, $W_2$ ... $W_n$ of the original target class feature model 326.

Figure 6:
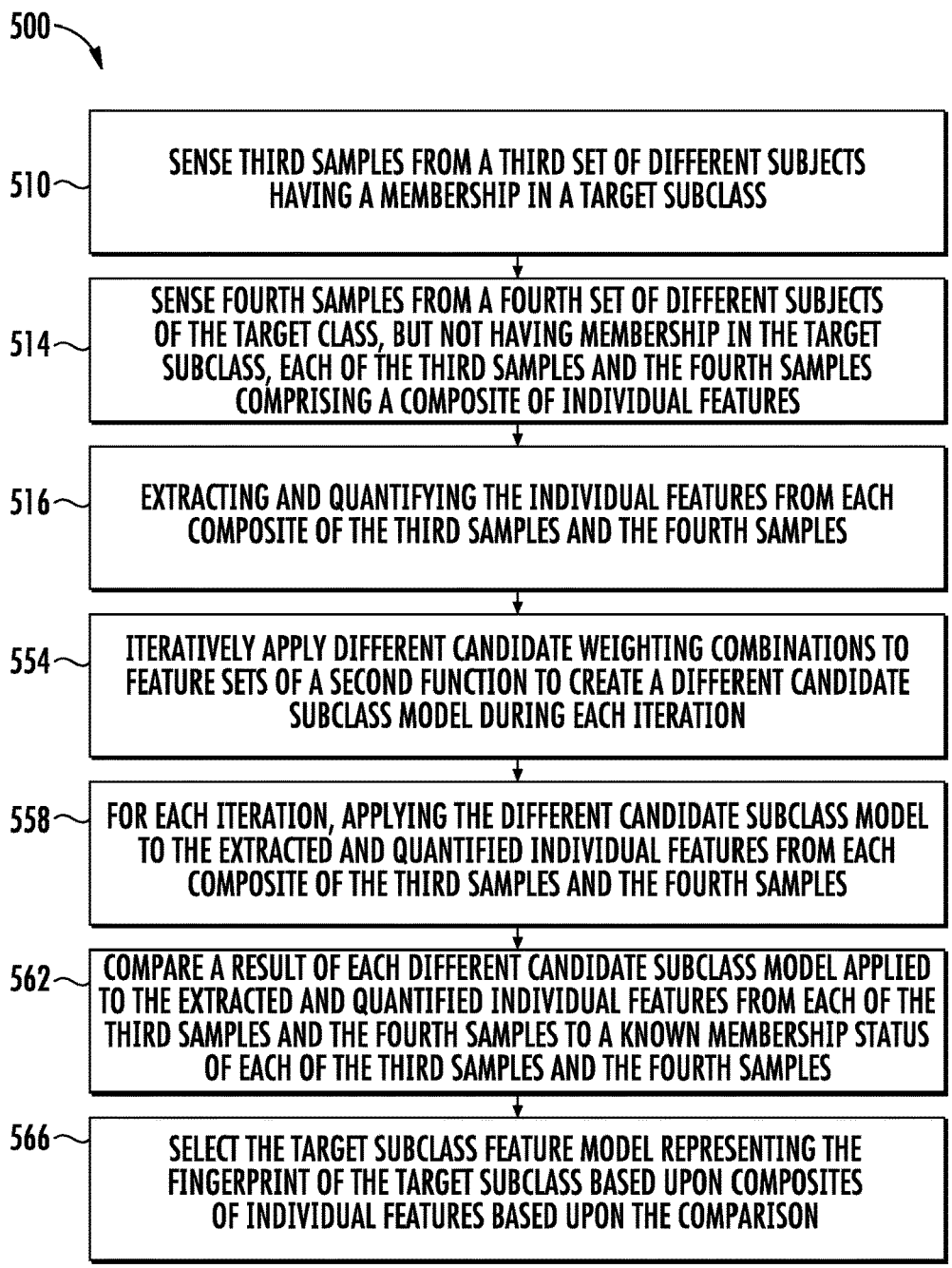
FIG. 6 is a flow diagram of an example method for generating a subclass feature model.

FIG. 6 is a flow diagram illustrating an example method 500 for generating a target subclass feature model. The subclass feature model generated by method 500 may provide additional insider detail as to a specific category of the larger class which membership was indicated by the application of the target class feature model 326. For example, rather than simply indicating whether or not a person has cancer, the target subclass feature model generated by method 500 may further indicate a subclass of the cancer determination such as a particular type of cancer or a particular stage of the cancer.

As illustrated by FIG. 6, method 500 mirrors methods 100 and 150 (described above) respect to generating a target class feature model. As indicated by block 510, third samples from a third set of different subjects having a membership in a target subclass are sensed. As indicated by block 514, fourth samples from a fourth set of different subjects of the target class, but not having membership in the target subclass are sensed. Each of the third samples and the fourth samples comprising a composite of individual features.

As indicated by block 516, the individual data features from each composite of the third samples and the fourth data samples are extracted and quantified. Thereafter, as indicated by block 554, different candidate weighting combinations are iteratively applied to feature sets of a subclass function to create a different candidate subclass model during each iteration.

As indicated by block 558, for each iteration, the different candidate subclass model is applied to the extracted and quantified individual features from each composite of the third samples and the fourth samples. As indicated by block 562, a result of each different candidate subclass model applied to the extracted and quantified individual features from each of the third samples and the fourth samples is compared to a known membership status of each of the third samples and the fourth samples with respect to the subclass. As indicated by block 566, the target subclass feature model representing the fingerprint of the target subclass based upon composites of individual features is selected are generated based upon the comparison. For example, the particular weighting combination having the fewest number of errors, the greatest accuracy, the least false positives or the least false negatives may be selected and incorporated into the subclass function, weighting each of the feature sets of the subclass function.

Figure 7:
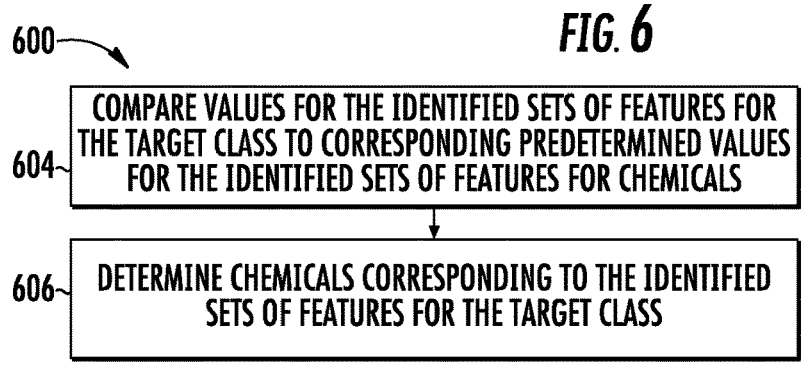
FIG. 7 is a flow diagram of an example method for determining chemicals corresponding to feature set of a target class feature model.
Figure 8:
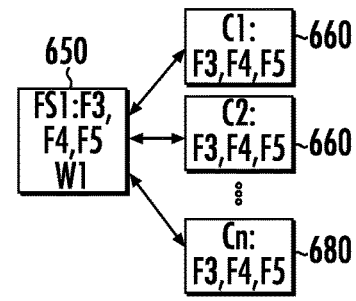
FIG. 8 is a diagram illustrating an example implementation of the method of FIG. 7.

FIGS. 7 and 8 are diagrams illustrating how the generated target class feature model 326, 426 or the target subclass generated pursuant to method 500 may be used to indicate not only those particular data sample features or data feature sets that highly indicate a condition or class membership but also may be used to indicate contributors that may be the root cause of the condition or class membership. For example, FIGS. 7 and 8 illustrate how chemicals linked to those features or feature sets that highly indicate a conditioner class membership may be identified. FIG. 7 is a flow diagram of an example method 600. FIG. 8 illustrates an example implementation of method 600.

As indicated by block 604 of FIG. 7, those feature sets in the target class feature module 326, 426 or the subclass feature model generated method 500 that have a high weighting factor, an associated weighting factor W above a predefined threshold may be identified as being especially indicative of an existing condition or class membership. The values for the particular feature sets for the target class/target subclass are compared to corresponding predetermined values for the same identified set of features for various possible contributors.

In the example shown in FIG. 8, feature set FS1 650 has been identified as a feature set in the target class feature model or the subclass feature model having a relatively high weighting factor $W_1$. In some implementations, feature set FS1 650 is identified in response to the weighting factor $W_1$ being above a predefined threshold. In the example illustrated, feature set $FS_1$ 650 has a value based upon a combination of three individual data features $F_3$, $F_4$ and $F_5$.

As further shown by FIG. 8 the weighted value of $FS_1$ is compared to the corresponding weighted value for the same feature set $FS_1$ obtained from samples from known compositions are differently known chemicals $C_1$-$C_n$ (660). For example, composition or chemical $C_1$ may be tested using the same testing procedure from which the ground truth samples were obtained. The features corresponding to the features of $FS_1$ are extracted and measured from the sample of the chemical $C_1$ (in this case, features $F_3$, $F_4$ and $F_5$). The values for these features extracted and quantified from the sample of the chemical $C_1$ are combined in the same fashion as the combination of the same features for $FS_1$ in the target class feature model/target subclass feature. The result of the combination of the features from the sample data from chemical $C_1$ are compared to results for the same feature set $FS_1$ using values from the ground truth samples. As indicated by block 606, a particular candidate chemical may be identified or determined as a chemical corresponding to the identified set of features $FS_1$ for the target class based upon the comparison. In other words, the particular chemical or group of chemicals that contribute to a particular condition or class membership may be identified.

Figure 9:
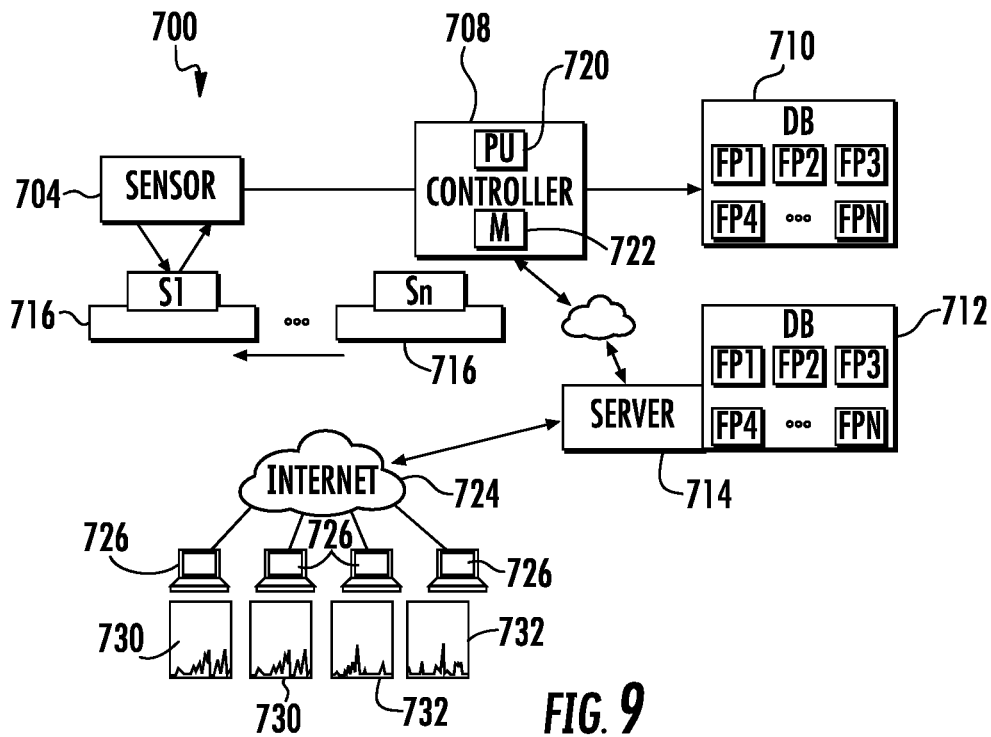
FIG. 9 is a schematic diagram of an example system for generating, using and communicating target class models.

FIG. 9 is a schematic diagram of an example system 700 for generating a target class feature model (as described above), for updating existing target class feature models and for providing a database that provides information to remote users regarding different target class feature models or fingerprints FP for different conditions or classes. System 700 comprises sensor 704, controller 708, local database 710, remote database 712 and server 714.

Sensor 704 comprises a device to sense or capture data from samples $S_1$-$S_n$ taken from subjects. Examples of such subjects from which a sample may be taken, include, but are not limited to, a person, an animal, a plant, a fluid, or an environmental body such as a lake, river, stream, ground or the like. In one implementation, sensor 704 may capture impedance data from a subject or physical sample flowing through a microfluidic device for microfluidic channel. In one implementation, sensor 704 may capture Raman spectroscopy data or surface enhanced Raman spectroscopy data. For example, in such an implementation, sensor 704 may impinge or direct light on to a subject or physical sample on a surface enhanced Raman spectroscopy stage or substrate 716, wherein the light reflected or scattered from the subject or physical sample on the substrate 716 is sensed by sensor 704 to produce a data sample, a spectra sample. In some implementations, the physical samples $S_1$-$S_n$ may be from the same subject but positioned on different SERS substrates 716. In one implementation, the physical samples and their associated or resulting sensed data samples are ground truth samples, known to belong to a target class or not belong to a target class.

Controller 708 comprises a processing unit 720 and a non-transitory memory 722. For purposes of this application, the term "processing unit" shall mean a presently developed or future developed computing hardware that executes sequences of instructions contained in a non-transitory memory. Execution of the sequences of instructions causes the processing unit to perform steps such as generating control signals. The instructions may be loaded in a random access memory (RAM) for execution by the processing unit from a read only memory (ROM), a mass storage device, or some other persistent storage. In other embodiments, hard wired circuitry may be used in place of or in combination with software instructions to implement the functions described. For example, controller 708 may be embodied as part of one or more application-specific integrated circuits (ASICs). Unless otherwise specifically noted, the controller is not limited to any specific combination of hardware circuitry and software, nor to any particular source for the instructions executed by the processing unit.

In the example illustrated, memory 722 contains instructions to direct the processing unit 720 to carry out any of the methods 100, 150, 200, 300, 400, 500 and 600 described above. For example, memory 722 may contain instructions to direct the processing unit 720 to create or generate multi-feature sets using the individual features identified in the collection of ground truth samples. These multi-feature sets may be used alone or in combination with individual features as part of candidate sample indicating functions. Memory 722 may further contain instructions direct the processing 722 iteratively apply different combinations of weightings to form different candidate sample indicating functions, wherein each of the different candidate sample indicating functions is applied to be measured or quantified results from the actual ground truth samples and wherein the results of each application are compared to evaluate the various different candidate sample indicating functions to identify and generate a target class (or subclass) feature model. Memory 722 further comprises instructions directing processing unit 720 to populate databases 710 and 712 with the various created or generated target class feature models and/or subclass class feature models, representing feature fingerprints FP of the respective classes/subclasses.

Databases 710 and 712 comprise a non-transitory computerize readable medium storing the previously generated and/or updated target class feature models and target subclass your models. Each database 710, 712 may comprise a class identifier and sets of sensed data features or feature sets, each set of sensed data features having the predetermined or selected weight or weighting factor (selected as described above with respect to block 230 in FIG. 3), wherein the weighting factor indicates the relevance of the feature set or set of data features towards identifying membership of a subject with respect to a class.

Server 714 provides wireless or network communication between controller 708 and remote database 712. Server 714 further provides access to remote database 712 across a wide area network or Internet 724 to remote users 726. Server 714 further facilitates communication between the remote users 726 and controller 708.

Server 714 facilitates communication of additional ground truth samples 730 from remote users 726 to controller 708, wherein controller 708 may update an existing target class feature model or subclass feature model using the additional ground truth samples as described above with respect to method 400. Server 714 further provides access to remote database 712, facilitating use of the stored fingerprints or generated target class feature models or subclass feature models by remote users 726. In one implementation, remote users 726 may retrieve and obtain a target class feature model or subclass feature model from database 712.

In another implementation, remote users 726 may upload a data sample 732 taken by the remote user of a subject to controller 708, wherein controller 708 extracts and quantifies those values of the individual features making up the feature sets that are at least most relevant to the determination of class membership. The extracted and quantified values taken from the sample uploaded by the remote user may then be applied or plugged into the corresponding target class feature model or subclass feature model, wherein the output of the model may be used by the controller 708 to provide information to the remote user as to whether the sample uploaded by the remote user indicates that the subject from which the sample was taken belongs to the particular class/subclass or possesses the particular condition in question.

Figure 10:
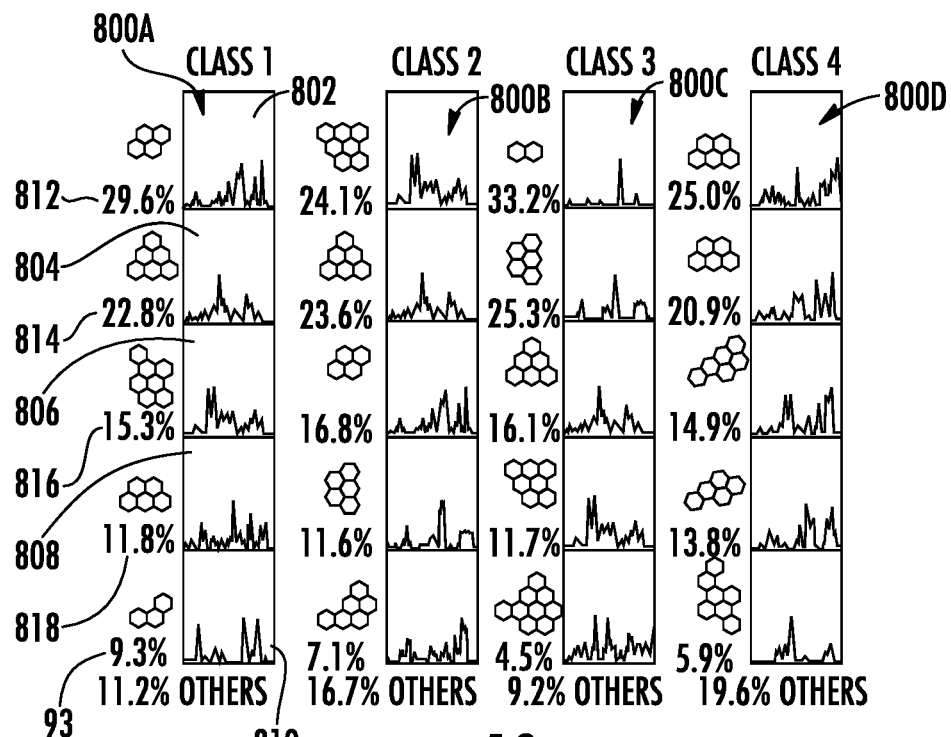
FIG. 10 is a diagram pictorially depicting various example target class feature models for different conditions or classes.

FIG. 10 is a diagram pictorially representing different target class feature models 800A, 800B, 800C and 800D (collectively referred to as models 800) for different classes Class 1, Class 2, Class 3 and Class 4, respectively, wherein the target class feature models 800 are based upon data features from SERS spectra data samples. The example individual features of the composite SERS spectra forming the different feature sets are pictorially represented. The target class feature model 800A for class 1 indicates that the feature set 802 has an associated weighting factor 812 of 29.6%, the features set 804 has an associated weighting factor 814 of 22.8%, the feature set 806 has an associated weighting factor 816 of 15.3%, the feature set 808 has an associated weighting factor 818 of 11.8% and the feature set 810 has an associated weighting factor of 9.3%, wherein all of the other feature sets ("Others"), combined, have a collective weight of 11.2%. Thus, for class 1, the generated target class feature model indicates that feature sets 802, 804 of the largest impact respect to indicating whether or not a sample belongs to a class. As described above with respect to method 600 in FIG. 7 8, such information may not only indicate what individual features are the most important for extraction and quantification when determining whether a sample has a condition or belongs to a class but may also assist in identifying what particular contributors or chemicals may be associated with the data features set and correspondingly, a contributor to the condition or class membership. As illustrated by 10, different target class feature models for different classes or conditions may have different weighting factors for the same feature sets extracted from samples taken by the same or similar sensing techniques or devices.

Although the present disclosure has been described with reference to example implementations, workers skilled in the art will recognize that changes may be made in form and detail without departing from the spirit and scope of the claimed subject matter. For example, although different example implementations may have been described as including one or more features providing one or more benefits, it is contemplated that the described features may be interchanged with one another or alternatively be combined with one another in the described example implementations or in other alternative implementations. Because the technology of the present disclosure is relatively complex, not all changes in the technology are foreseeable. The present disclosure described with reference to the example implementations and set forth in the following claims is manifestly intended to be as broad as possible. For example, unless specifically otherwise noted, the claims reciting a single particular element also encompass a plurality of such particular elements. The terms "first", "second", "third" and so on in the claims merely distinguish different elements and, unless otherwise stated, are not to be specifically associated with a particular order or particular numbering of elements in the disclosure.

What is claimed is:

1. A method comprising:
    sensing first data samples from a first set of different subjects having a membership in a target class;
    sensing second data samples from a second set of different subjects not having a membership in the target class, each of the first data samples and the second data samples comprising a composite of individual data features;
    extracting and quantifying the individual data features from each composite of the first data samples and the second data samples; and
    identifying sets of data features and associated weightings of a target class feature model based upon quantified values of the individual data features from each composite of the first data samples and the second data samples to create a target class feature model representing a fingerprint of the target class to determine membership status of a sample having an unknown membership status with respect to the target class, wherein the identification of sets of data features and associated weightings of a target class model comprises:
    iteratively applying different candidate weighting combinations to data feature sets of a function to create a different candidate model during each iteration;
    for each iteration, applying the different candidate model to the extracted and quantified individual features from each composite of the first data samples and the second data samples;
    comparing a result of each different candidate model applied to the extracted and quantified individual data features from each of the first data samples and the second data samples to a known membership status of each of the first data samples and the second data samples; and
    selecting the target class feature model representing the fingerprint of the target class based upon composites of individual data features based upon the comparison, wherein the first data samples and the second data samples comprise SERS spectra data and wherein the sets of data features comprise features based upon spectral peaks of the SERS spectra data.

2. The method of claim 1, wherein the first data samples and the second data samples comprise SERS spectra data of a subject taken with different Raman spectroscopy enhancement surfaces.

3. The method of claim 1, the first data samples and the second data samples comprise impedance data.

4. The method of claim 1 further comprising creating multi-feature feature sets for the function.

5. The method of claim 1 further comprising storing the identified sets and assigned weights to a target class as part of a database.

6. The method of claim 1, wherein at least one of the different candidate sets of individual data features comprises a single data feature.

7. The method of claim 1 further comprising:
    receiving an additional data sample having a known membership status with respect to the target class;
    extracting and quantifying the individual data features from the composite of the additional sample;

applying the selected target class feature model to the extracted and quantified individual data features from the additional sample;

comparing a result of the selected target class feature model applied to the extracted and quantified individual data features from the additional data sample to the known membership status; and based upon the result of the comparison:

iteratively applying different candidate weighting combinations to the feature sets of the function to create different candidate models for identifying membership status of a sample with respect to the target class;

for each iteration, applying the different candidate model to the extracted and quantified individual data features from each composite of the first data samples, the second data samples and the additional sample;

comparing a result of each different candidate model applied to the extracted and quantified individual data features from each of the first data samples and the second data samples to a known membership status of each of the first data samples, the second data samples and the additional data sample; and selecting a new target class feature model representing the fingerprint of the target class based upon composites of individual features based upon the comparison.

8. The method of claim 1, wherein the first data samples and the second data samples comprise SERS spectra and wherein the multiple features comprise features selected from a group of features consisting of: maximum peak amplitude, peak amplitude at a predetermined time; a statistical value based upon a plurality of peak characteristics; peak to peak ratio; maximum peak amplitude, peak amplitude at a predetermined time, a statistical value based upon a plurality of peak characteristics, a peak to peak ratio.

9. The method of claim 1 further comprising:

sensing a sample having an unknown membership status with respect to target class;

extracting and quantifying a portion of individual features of a composite of individual features of the sample having the unknown membership status, the portion of individual features comprising those individual features making up the feature sets of the target class;

applying the target class model to the extracted and quantified portion of individual data features; and determining a membership status of the data sample based upon a result of the application of the target class feature model to the extracted and quantified portion of individual data features.

10. The method of claim 1 further comprising:

sensing third data samples from a third set of different subjects having a membership in a target subclass;

sensing fourth data samples from a fourth set of different subjects of the target class, but not having membership in the target subclass, each of the third data samples and the fourth data samples comprising a composite of individual data features;

extracting and quantifying the individual data features from each composite of the third data samples and the fourth data samples;

iteratively applying different candidate weighting combinations to feature sets of a second function to create a different candidate subclass model during each iteration;

for each iteration, applying the different candidate subclass model to the extracted and quantified individual features from each composite of the third samples and the fourth samples;

comparing a result of each different candidate subclass model applied to the extracted and quantified individual features from each of the third samples and the fourth samples to a known membership status of each of the third samples and the fourth samples; and selecting the target subclass feature model representing the fingerprint of the target subclass based upon composites of individual features based upon the comparison.

11. The method of claim 1 further comprising:

comparing the weighted sets of features of the target class model to corresponding predetermined sets of features for chemicals; and determining chemicals contributing to membership in the target class based upon the comparison.

12. An apparatus comprising:

a non-transitory computer-readable medium containing instructions to direct a processor to:

receive a composite of data features from each data sample of first data samples having a membership in a target class;

receiving a composite of data features from each data sample of second data samples not having a membership in the target class;

extract and quantify individual data features from each composite of the first data samples and the second data samples;

iteratively apply different candidate weighting combinations to feature sets to create a different candidate model during each iteration;

for each iteration, apply the different candidate model to the extracted and quantified individual features from each composite of the first data samples and the second data samples;

compare a result of each different candidate model applied to the extracted and quantified individual features from each of the first data samples and the second data samples to a known membership status of each of the first data samples and the second data samples; and select the target class feature model representing the fingerprint of the target class based upon composites of individual features based upon the comparison, wherein the first data samples and the second data samples comprise SERS spectra data and wherein the feature sets comprise features based upon spectral peaks of the SERS spectra data.

13. The apparatus of claim 12, wherein the features based upon spectral peaks of the SERS spectra data comprise features selected from a group of features consisting of: maximum peak amplitude, peak amplitude at a predetermined time; a statistical value based upon a plurality of peak characteristics; peak to peak ratio; maximum peak amplitude; peak amplitude at a predetermined time; a statistical value based upon a plurality of peak characteristics; and a peak to peak ratio.

14. A method comprising:

sensing first data samples from a first set of different subjects having a membership in a target class;

sensing second data samples from a second set of different subjects not having a membership in the target class, each of the first data samples and the second data samples comprising a composite of individual data features;

extracting and quantifying the individual data features from each composite of the first data samples and the second data samples; and identifying sets of data features and associated weightings of a target class feature model based upon quantified values of the individual data features from each composite of the first data samples and the second data samples to create a target class feature model representing a fingerprint of the target class to determine membership status of a sample having an unknown membership status with respect to the target class, wherein the first data samples and the second data samples comprise SERS spectra data and wherein the sets of data features comprise features based upon spectral peaks of the SERS spectra data, wherein the first data samples and the second data samples comprise SERS spectra data of a subject taken with different Raman spectroscopy enhancement surfaces.

15. The method of claim 14, wherein the features based upon spectral peaks of the SERS spectra data comprise features selected from a group of features consisting of: maximum peak amplitude, peak amplitude at a predetermined time; a statistical value based upon a plurality of peak characteristics; peak to peak ratio; maximum peak amplitude, peak amplitude at a predetermined time, a statistical value based upon a plurality of peak characteristics, a peak to peak ratio.

16. The method of claim 14, wherein the identification of sets of data features and associated weightings of a target class model comprises:
iteratively applying different candidate weighting combinations to data feature sets of a function to create a different candidate model during each iteration;
for each iteration, applying the different candidate model to the extracted and quantified individual features from each composite of the first data samples and the second data samples;
comparing a result of each different candidate model applied to the extracted and quantified individual data features from each of the first data samples and the second data samples to a known membership status of each of the first data samples and the second data samples; and
selecting the target class feature model representing the fingerprint of the target class based upon composites of individual data features based upon the comparison.

17. The method of claim 14 further comprising:
sensing third data samples from a third set of different subjects having a membership in a target subclass;
sensing fourth data samples from a fourth set of different subjects of the target class, but not having membership in the target subclass, each of the third data samples and the fourth data samples comprising a composite of individual data features;
extracting and quantifying the individual data features from each composite of the third data samples and the fourth data samples;
iteratively applying different candidate weighting combinations to feature sets of a second function to create a different candidate subclass model during each iteration;
for each iteration, applying the different candidate subclass model to the extracted and quantified individual features from each composite of the third samples and the fourth samples;
comparing a result of each different candidate subclass model applied to the extracted and quantified individual features from each of the third samples and the fourth samples to a known membership status of each of the third samples and the fourth samples; and
selecting the target subclass feature model representing the fingerprint of the target subclass based upon composites of individual features based upon the comparison.

* * * * *